United States Patent [19]

Langlois et al.

[11] 4,351,338

[45] Sep. 28, 1982

[54] VAGINAL TAMPON

[76] Inventors: Pierre Langlois, 24, rue de Clichy, 75009 Paris; Marc Mollet, 38, rue des Chevaliers de Saint Jean, 91100 Corbeil, both of France

[21] Appl. No.: 151,893

[22] Filed: May 21, 1980

[51] Int. Cl.³ .............................................. A61F 13/20
[52] U.S. Cl. ...................................... 128/285; 128/270
[58] Field of Search ................ 128/285, 270, 127, 128

[56] References Cited

U.S. PATENT DOCUMENTS 3,108,043 10/1963 Hillman et al. ..................... 128/270
3,762,414 10/1973 Burnhill .
3,916,898 11/1975 Robinson ........................... 128/270
3,918,452 11/1975 Cornfeld .

Primary Examiner—George F. Lesmes
Assistant Examiner—B. K. Johnson
Attorney, Agent, or Firm—Cushman, Darby & Cushman

[57] ABSTRACT

A vaginal tampon is disclosed which is made out of a cellular material having semi-open cells and impregnated with a compound of a contraceptive composition and of a delaying medium having gelifying properties when moistened by internal secretions and by preliminary dipping within water, the tampon thus swelling to realize an efficient mechanical barrier while the dry compound is progressively and durably released.

15 Claims, 2 Drawing Figures

U.S. Patent  Sep. 28, 1982  4,351,338

VAGINAL TAMPON

BACKGROUND OF THE INVENTION

The present invention relates to novel contraceptive means and more specifically to a vaginal tampon impregnated with contraceptive spermicidal composition.

DESCRIPTION OF THE PRIOR ART

In addition to the mechanical contraceptive means of the vaginal or intra-uterine type, different temporary contraceptive means are known which make use of spermicidal compositions in the form of creams or gels conditioned in distributing tubes or in capsules. With such a conditioning, a convenient application of the gel or the cream is frequently difficult or unsatisfactory, and in any case, the thus applied spermidical composition is submitted to an excessive solubility affecting considerably the efficiency thereof. On the other hand, with such a conditioning, the application of the spermicidal medium, which is achieved by the finger, may induce risks of contamination, when the conditioning in the form of capsules additionally raises problems of storage in hermetic cells.

SUMMARY OF THE INVENTION

A general feature of the present invention is to avoid and overcome the foregoing difficulties by the provision of contraceptive means of a compact configuration including a spermicidal composition impregnating an improved cellular support which permits an easy and efficient insertion in the body while ensuring a progressive, durable and controlled releasing of the spermicidal composition so as to combine in an improved manner the effects of both mechanical and spermicidal contraceptive means.

More specifically, a feature of the present invention is to provide a vaginal tampon comprising a synthetic sponge member out of a semi-open cell cellular material impregnated with a compound of a spermicidal agent and of a delaying medium.

According to another feature of the invention, a string in the form of a loop is provided for easy removal of the tampon.

It is still another feature of the invention to provide a tampon normally presented in a compressed configuration, the impregnation compound therein being in a dried state.

The vaginal tampon or sponge of a cellular material having semi-open cells impregnated with a compound of a spermicidal agent and of a delaying medium adapted to form a gel when being moistened provides for a vaginal appliance which is simple to manufacture, store and handle, which can be easily inserted within the body wherein, under the effect of the internal secretions, realizes an immediate swelling for a convenient adaptation to the geometry of the vagina and for occulting the cervix of the uterus while providing for an immediate but continuous, progressive and durable releasing of the spermicide agent so as to submit the ejaculated spermatozoides to a mechanical barrier and to a continuous bio-chemical action resulting in an improved efficiency of the tampon.

According to yet another feature of the invention, the string made of a non-wicking string has the form of a closed loop, the knot of which is embedded within the bulk of the sponge material, the main portion of the loop extending out of the tampon of a distance not greater than about 5 cm, whereby inducing no detrimental effect during copulation and facilitating easy extraction thereof by a finger.

Still another feature of the present invention is to provide an applicator means for housing the impregnated tampon with a view of moistening same and easy insertion thereof.

DETAILED DESCRIPTION OF THE INVENTION

The aforesaid features and others will become apparent from the following description made in reference with the accompanying drawings, wherein.

PREFERRED EMBODIMENTS OF THE INVENTION

Figure 1:
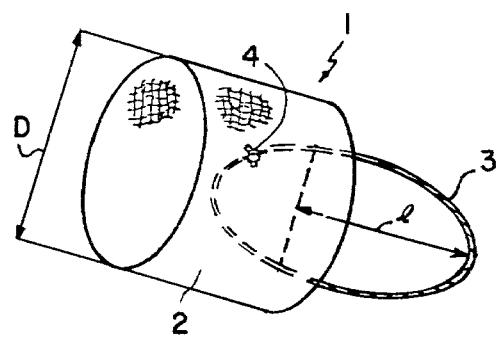
FIG. 1 is a perspective view of a tampon in accordance with the invention.

There is shown in FIG. 1 a tampon according to the present invention, which is generally designated by reference 1 and comprises a body 2 out of a cellular material, having semi-open cells and preferably including essentially semi-open cells, which is impregnated with a compound of a spermicidal composition and of a delaying medium having gelifying properties when moistened and, optionally, of additives authorized in pharmaceutics and including for instance antiseptic agents. The body or sponge member 2 is made out of a plastic material compatible with the body and more particularly with the vaginal mucus and includes pores having dimensions comprised between about 0.5 mm and 1 mm.

The sponge member 2 is conferred an anatomic shape so as to be conveniently received within the vagina adjacent the uterus cervix without the tendency of occupying an off-set position so as not to inconvenience the woman or the penis of the partner during copulation. Preferably, the sponge member 2 has a spherical shape or pseudo-spherical shape with an intermediate cylindrical portion but, practically, for manufacturing purposes, the sponge member, as illustrated in FIG. 1, has advantageously the form of a thick cylinder having a height close to the diameter D in the expanded configuration of the tampon, said diameter D being comprised between about 4 cm and 4.5 cm. In a specific embodiment of the invention, the tampon 1 is normally presented in a compressed configuration which makes easier its insertion within the vagina, moistening and impregnation thereof by the vaginal secretions causing same to rapidly fully expand after location within the vagina.

To allow easy extraction of the tampon, there is further provided an extraction means 3 consisting in a non-wicking string out of cotton or polyamide fibers. According to a feature of the invention, the string 3 is in the form of a closed loop, the closing knot being embedded within the bulk of the sponge member 2, whereby a main portion of the loop extends outwardly from one end of the tampon. In a preferred embodiment, the maximum sag l of the free outer portion of the loop is comprised between about 3 and 5 cm.

The cellular material of the sponge member 3 may be made out of fibrine or of expanded polyethylene having a low or medium molecular weight, comprised between 15,000 and 35,000 and totally devoid or residues of foaming agent. In a preferred embodiment, the sponge member 2 is made out of polyvinyle formal or polyvinilic alcohol rendered insoluble with formol and rinsed. Said latter materials are advantageous in that they provide for sinuous intricate internal communication paths between the semi-open cells in the sponge, whereby lowering emission of the gelified active agents contained in the tampon and adding to the delay releasing action of the delaying medium, and in that, when compressed, the sponge member retains durably its compressed configuration when not moistened, and rapidly swells when moistened.

The spermicidal composition in the compound impregnating the sponge member comprises steroidal or non-steriodal agents, such as benzethonium chloride or phenyl-mercury nitrate and includes preferably alkyl-benzalkonium. The delaying medium having a gelifying action when moistened for time delaying releasing of the spermicidal agent and prolongating the action thereof is advantageously a sterile gel of carboxymetlyl cellulose stabilized by a conservator such as methyl-parahydroxybenzoate.

The manufacture of the contraceptive tampon in accordance with the invention is the following: The sponge member 2 is shaped, e.g. by molding the cellular material, sterilized in a sterilizer with a sterilizing gas or a convenient irradiation, and the sterilized sponge member is impregnated with the above mentioned compound by immersing same within a solution of said compound, the impregnated sponge member being slightly squeezed if necessary. The impregnated sponge member is dried, for example lyophilized by being frozen and sublimated. The sponge member with its dried impregnating compound may be ulteriorly compressed for easy direct insertion within the vagina.

The thus realized tampon is imputrescible to the organic secretions, is heat- and cold-proof by reason of its dried condition, is not resorbable and is, neutral and compatible with the tissues of the vaginal mucus. With respect to the latter, the tampon does not show any adhering tendency and its flexibility when expanded makes its practically imperceivable by the woman or her partner.

Figure 2:
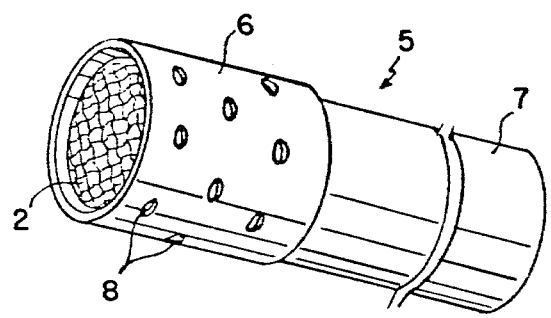
FIG. 2 is a perspective view of an applicator for a tampon in accordance with the invention.

The tampon in its dry and eventually pre-compressed condition may be stored or momentarily inserted within the applicator illustrated in FIG. 2. Said applicator 5 comprises a cylindrical housing tube 6 wherein the sponge member 2 is arranged in a compressed condition and a pushing tube 7, the housing tube 6 further advantageously comprising holes or openings 8 formed within the lateral wall. It is thus possible, with such an applicator, to preliminarily dip the housing cylindrical tube 6 containing the tampon 2 within water for moistening same and achieving a pre-expansion of the cellular material of the sponge member 2, the sponge member 2, the introduction and setting of the tampon being made in a conventional manner, whereby the thus initiated swelling thereof makes same quasi immediately efficient, independently of the amount of the internal secretions of the woman. The tampon is thus operative less than one minute after its insertion, its contraceptive action being prolongated over a period of at least 5 hours.

Although the present invention has been disclosed with reference to preferred embodiments, other embodiments and modifications may be contemplated without departing from the spirit and scope of the invention.

What is claimed is:

1. A vaginal contraceptive tampon, comprising a synthetic sponge member made of a cellular material having semi-open cells and impregnated with a compound of a spermicidal composition and of a delaying medium having gelifying properties when moistened;
   the semi-open cells providing only sinuous intricate internal communication paths among the cells and to exterior, thereby lowering emission of the compound when gelified and acting to delay releasing action of the delaying medium and due to which the sponge member, if compressed in a not-moistened condition remains more durably compressed yet rapidly swells when moistened, all in comparison with the same sponge member if made of open cell foam.

2. The tampon of claim 1, wherein said sponge member is made out of polyvinyl formal.

3. The tampon of claim 2, wherein said sponge member is normally in a compressed formed configuration.

4. The tampon of claim 3, wherein said impregnating compound and said sponge member are prealably dried before said sponge member is compressed.

5. The tampon of claim 1, wherein said sponge member is made out of expanded polyethylene having a molecular weight comprised between about 15,000 and 30,000 and devoid of any residues of foaming agents.

6. The tampon of claim 1, wherein said sponge member and said impregnating compound are normally in a dried condition.

7. The tampon of claim 1, wherein said delaying medium comprises a sterile gel of carboxymethyl cellulose.

8. The tampon of claim 7, wherein said spermicidal composition comprises alkylbenzenkonium.

9. The tampon of claim 1, wherein said sponge member has the form of a thick cylinder, the diameter of said sponge member in its expanded state being comprised between 4 and 4.5 cm.

10. The tampon of claim 1, further comprising an extracting means connected to said sponge member and consisting in a non-wicking string.

11. The tampon of claim 10, wherein said string is in the form of a closed loop, a portion of which extends outwardly from said sponge member, the binding knot of said string being embedded within the bulk of said sponge member.

12. The tampon of claim 1, further associated with a tubular applicator within which it is received in a compressed condition.

13. The combination of claim 12, wherein the peripheral wall of said applicator is formed with openings.

14. A method of contraception utilizing a tampon comprising a sponge member out of a cellular material having semi-open cells impregnated with a dried compound of a spermicidal composition and of a delaying medium having gelifying properties when moistened, which comprises the steps of dipping said tampon within water prior to insertion within the vagina.

15. A method of manufacturing the tampon of claim 3, comprising the steps of form shaping and sterilizing said sponge member, preparing the gelifying compound of said spermicidal composition and of said sterilized delaying medium, impregnating the sterilized sponge member with said compound, drying the impregnated sponge member in a drying process, and compressing said impregnated and dried sponge member.

* * * * *